United States Patent
Ikeda et al.

(10) Patent No.: US 6,861,132 B2
(45) Date of Patent: Mar. 1, 2005

(54) POROUS POLYPROPYLENE FILM, PROCESS FOR PRODUCING THE SAME, AND ABSORBENT ARTICLE EMPLOYING THE FILM

(75) Inventors: Naoki Ikeda, Kyoto (JP); Kiyoshi Sadamitsu, Kyoto (JP); Manabu Hoki, Kyoto (JP); Kenichiro Nagata, Kyoto (JP); Toshiaki Kobayashi, Kyoto (JP)

(73) Assignee: New Japan Chemical Co., Ltd., Kyoto (JP)

( * ) Notice: Subject to any disclaimer, the term of this patent is extended or adjusted under 35 U.S.C. 154(b) by 172 days.

(21) Appl. No.: 10/275,987

(22) PCT Filed: Jun. 1, 2001

(86) PCT No.: PCT/JP01/04669

§ 371 (c)(1),
(2), (4) Date: Nov. 20, 2002

(87) PCT Pub. No.: WO01/92386

PCT Pub. Date: Dec. 6, 2001

(65) Prior Publication Data

US 2003/0148091 A1 Aug. 7, 2003

(30) Foreign Application Priority Data

Jun. 2, 2000 (JP) ........................ 2000-166023

(51) Int. Cl.[7] .......................... B32B 5/22; B32B 31/00; C08K 5/20
(52) U.S. Cl. ................ 428/317.9; 524/229; 524/214; 564/152; 564/155; 564/180; 156/229; 604/358
(58) Field of Search .................. 428/317.9; 524/229, 524/214; 564/152, 155, 180; 156/229; 604/358

(56) References Cited

U.S. PATENT DOCUMENTS

| | | | |
|---|---|---|---|
| 5,310,584 A | 5/1994 | Jacoby et al. ............... | 428/2 |
| 6,015,764 A | 1/2000 | McCormack et al. ....... | 442/370 |
| 6,235,823 B1 * | 5/2001 | Ikeda et al. ................. | 524/229 |

FOREIGN PATENT DOCUMENTS

| | | |
|---|---|---|
| EP | 632 095 | 1/1995 |
| GB | 2 251 205 | 7/1992 |
| JP | 62-195030 | 8/1987 |
| JP | 63-199742 | 8/1988 |
| JP | 2-311539 | 12/1990 |
| JP | 6-100720 | 4/1994 |
| JP | 7-118429 | 5/1995 |
| JP | 8-3353 | 1/1996 |
| JP | 9-176352 | 7/1997 |
| JP | 9-255804 | 9/1997 |
| JP | 2000-169608 | 6/2000 |
| TW | 341516 | 1/1998 |
| WO | 90/11321 | 10/1990 |

OTHER PUBLICATIONS

Chu, et al., "Microvoid formation process during the plastic deformation of β–form polypropylene," Polymer, vol. 35, No. 16, pp. 3442–3448 (1994).
PCT International Preliminary Examination Report, Jun. 28, 2002; translation.
Taiwanese Office Action dated Aug. 28, 2003.

* cited by examiner

Primary Examiner—Terrel Morris
Assistant Examiner—Hai Vo
(74) Attorney, Agent, or Firm—Armstrong, Kratz, Quintos, Hanson & Brooks, LLP (57) ABSTRACT

Disclosed is a porous film made of a resin composition containing (I) (i) a propylene-ethylene copolymer or (ii) a polypropylene-based resin mixture containing a propylene-ethylene copolymer, each having an ethylene content of 3.0 to 7.0 wt. % and an MFR measured at 230° C. of 2.0 to 4.0 g/10 min and (II) a β-crystal nucleating agent; the film having a porosity of 20 to 80%, a Gurley air permeability of 5,000 sec/100 cc or lower as measured according to JIS P-8117, a water vapor permeability of 2,000 g/m²·24 h or higher as measured according to JIS Z-0208 and a water pressure resistance of 75 kPa or higher as measured according to JIS L-1092 using an aqueous surfactant solution; a process for producing the same; and an absorbent article employing the porous film as a backsheet.

17 Claims, 1 Drawing Sheet

Fig. 1

POROUS POLYPROPYLENE FILM, PROCESS FOR PRODUCING THE SAME, AND ABSORBENT ARTICLE EMPLOYING THE FILM

TECHNICAL FIELD

This invention relates to a porous polypropylene film having numerous fine, continuous through-pores, especially a porous polypropylene film with excellent breathability and continuous through-pores, which is suitable for use as a backsheet for absorbent articles; and to a process for producing the film; and to an absorbent article employing the porous film as a backsheet.

BACKGROUND ART

Commonly and widely used disposable diapers comprise an absorbing material that absorbs excreta such as urine and the like, a topside material that covers one surface of the absorbing material and touches the wearer's skin, and a backside material that covers the absorbing material and prevents leakage of fluid excreta. The diaper is formed by bonding these materials. Such a disposable diaper has an elastic means provided to prevent excreta from leaking out beyond the waist or leg region and a closure means, such as a closure tape, which is used to fasten the diaper on the front and rear waist regions when wearing the diaper.

As such a backside material, a polyolefin-based porous film having breathability and water vapor permeability is known. However, when the diaper is put on incorrectly or when the closure tape is peeled off to check for urination while the diaper is being worn, backside materials formed using porous film with insufficient strength have a problem of breakage, making it necessary to change the diaper for a new one. In the field of diapers for adults, the problem of insufficient leakage prevention exists in addition to the insufficient strength of the diapers, and the strength and leakage prevention properties of the diapers have actually been increased at the cost of breathability and water vapor permeability.

Thus, as a means for obviating the aforementioned drawbacks, a porous film having excellent breathability and water vapor permeability as well as improved strength and leakage prevention is strongly desired.

Polypropylene occurs in crystal states such as $\alpha$ crystals and $\beta$ crystals. Under general crystallization conditions, $\alpha$ crystals, which are the most stable, are mainly produced, but $\beta$ crystals can be produced preferentially by employing specific crystallization conditions or adding a $\beta$-crystal nucleating agent. Also, $\beta$ crystals are known to undergo a crystal transformation into stable $\alpha$ crystals when subjected to thermal and mechanical action, and recently several methods have been proposed for producing a porous film, especially a breathable polypropylene film having continuous through-pores, which utilize the crystal transformation that occurs in the course of stretching (Japanese Unexamined Patent Publications Nos. 118429/1995, 176352/1997, 255804/1997 and 100720/1994).

The process for forming continuous through-pores is not yet fully clarified. However, various processes have been hypothesized as follows. Formation of as many $\beta$ crystals as possible in an unstretched web sheet before stretching and subsequent stretching of the sheet causes a crystal transformation from $\beta$ crystals into $\alpha$ crystals. In the course of the stretching, the transformation from $\beta$ crystals with low crystal density to $\alpha$ crystals with high crystal density causes volume shrinkage and leads to exfoliation at the crystal surface, whereby pores are formed in the initial stage of stretching. Another possibility is that pores are formed by exfoliation at the crystal surface resulting from the difference in stretchability between $\alpha$ crystals and $\beta$ crystals before the transformation into $\alpha$ crystals. Moreover, another possibility suggested is that crystal fineness, orientation and re-arrangement may participate in the pore formation. It is considered that, as the stretching process progresses thereafter, the size of the pores becomes gradually larger and adjacent pores are connected to each other, resulting in the formation of continuous through-pores.

Each publication mentioned above suggests the necessity of forming as many $\beta$ crystals as possible in an unstretched web sheet before stretching it as a condition for obtaining a breathable film. As an index of the $\beta$-crystal content or proportion of $\beta$-crystals in the unstretched web sheet, a K value determined by X-ray diffraction measurement is employed. That is, the higher the K value is, the easier it is to obtain a film with good breathability. Thus, for example, Japanese Unexamined Patent Publication No.255804/1997 recommends that the K value be not less than 0.7, and preferably 0.8 to 0.98. However, it is known that by incorporating a certain $\beta$-crystal nucleating agent, the recommended K values can be achieved relatively easily without employing special crystallization conditions, and moreover, as will be described below, even a high K value does not necessarily result in a production of a film with excellent breathability.

For example, Japanese Unexamined Patent Publication No.176352/1997 discloses that a single use of a $\beta$-crystal nucleating agent cannot produce a film with sufficient breathability in spite of a high K value, and proposes a method for removing the drawbacks, which comprises adding and mixing particles of other resins than polypropylene. However, it is difficult to uniformly disperse these resin particles in the polypropylene resin, and the uneven dispersion tends to cause the films to break in the stretching step, and the films produced by the method are not preferable from the standpoint of recycling.

DISCLOSURE OF THE INVENTION

An object of the present invention is to provide a porous polypropylene film, specifically, a porous polypropylene film with excellent breathability and continuous through-pores that is suitable for use as a backsheet for absorbent articles; and a process for producing the film; and an absorbent article with a backsheet made of the porous film with excellent breathability, water vapor permeability and good texture as well as excellent strength and leakage prevention.

The present inventors conducted extensive researches in light of the above problems and, as a result, discovered that a high content of thermally stable $\beta$-crystals in an unstretched web sheet before stretching is important to produce an excellent porous film.

Kimura et al. discloses that $\beta$ crystals include thermally stable $\beta$ crystals ($\beta$1 crystals) and metastable $\beta$ crystals ($\beta$2 crystals), and that $\beta$2 crystals tend to undergo transformation into $\alpha$ crystals at a lower temperature than $\beta$1 crystals and their contribution to pore formation is smaller (POLYMER Vol. 35 No. 16 1994). The K value is a ratio of the combined amount of $\beta$1 crystals and $\beta$2 crystals to the total amount of all polypropylene crystals, and therefore a high $\beta$2-crystal content does not result in a film with excellent breathability even if the K value is high. Also, since the ratio of $\beta$1-crystal content to β2-crystal content varies depending on crystallization conditions and not depending on the K value, the β1-crystal content cannot be determined from the K value.

The present inventors carried out research for the purpose of obtaining a porous film having excellent physical properties by increasing the β1-crystal content. As a result, the inventors found that a β-crystal nucleating agent-containing, polypropylene-based resin composition having a specific melt flow rate and ethylene content, wherein the proportion of the β1 crystal relative to the total amount of all crystals and the β1-crystal heat of fusion per unit weight of the resin composition are within a specified range, can be advantageously used for producing a porous polypropylene-based resin film, and that the thus obtained porous polypropylene film comprising a polypropylene-based resin and a β-crystal nucleating agent has more excellent mechanical strength than porous films of known polyethylene-based resins and moreover has many through-pores with a finer pore diameter, as compared with porous films prepared by stretching filler-containing compositions, thereby achieving the desired objects of improving mechanical strength and leakage prevention while exhibiting outstanding breathability and water vapor permeability. The present invention was completed based on these findings and further research.

Specifically, the present invention provides the following inventions.

1. A porous polypropylene film with excellent breathability and continuous through-pores, the film being prepared from a polypropylene-based resin composition comprising (I) (i) a propylene-ethylene copolymer having an ethylene content of 3.0 to 7.0 wt. % and a melt flow rate (MFR, JIS K-6857) of 2.0 to 4.0 g/10 min as measured at 230° C., or
(ii) a polypropylene-based resin mixture containing a propylene-ethylene copolymer, the mixture having an ethylene content of 3.0 to 7.0 wt. % and a melt flow rate (MFR, JIS K-6857) measured at 230° C. of 2.0 to 4.0 g/10 min and
(II) a β-crystal nucleating agent; and the film having a porosity of 20 to 80%, a Gurley air permeability measured according to JIS P-8117 of 5,000 sec/100 cc or lower, a water vapor permeability of 2,000 g/m$^2$·24 h or higher as measured according to JIS Z-0208 and a water pressure resistance of 75 kPa or higher as measured according to JIS L-1092 except that an aqueous surfactant solution is used instead of pure water.

2. The porous polypropylene film according to Item 1 above, which has a thickness of 5 to 50 μm and a mechanical strength of 40 MPa or higher as measured according to JIS K-7127.

3. The porous polypropylene film according to Item 1 above, which is prepared by stretching an unstretched web sheet wherein the β1-crystal content, i.e., the proportion of thermally stable β crystals (β1 crystals) relative to the total amount of all crystals is 65% or higher, and the β1-crystal heat of fusion per unit weight of the unstretched web sheet is 50 J/g or higher, as determined by differential scanning calorimetry (DSC).

4. The porous polypropylene film according to Item 1 above, wherein at least one component of the polypropylene-based resin mixture containing a propylene-ethylene copolymer is a polypropylene resin having a weight average molecular weight (Mw) of $10^5$ to $10^6$ as determined by gel permeation chromatography (GPC) and a melt flow rate (MFR, JIS K-6857) measured at 230° C. of 0.5 to 10.0 g/10 min.

5. The porous polypropylene film according to Item 1 above, wherein the polypropylene-based resin mixture containing a propylene-ethylene copolymer is composed of a mixture of at least two members of polypropylene-based resins selected from the following resins (A), (B) and (C):

(A) a polypropylene-based resin having an MFR of 0.1 to 2.0 g/10 min;
(B) a polypropylene-based resin having an MFR of more than 2.0 g/10 min and less than 4.0 g/10 min;
(C) a polypropylene-based resin having an MFR of 4.0 to 10.0 g/10 min;

the mixture having an ethylene content of 3.0 to 7.0 wt. % and a melt flow rate (MFR, JIS K-6857) measured at 230° C. of 2.0 to 4.0 g/10 min; and at least one component of the mixture being a propylene-ethylene copolymer.

6. The porous polypropylene film according to Item 5 above, wherein the polypropylene-based resin mixture comprises 10 to 35 wt. % of resin (A), 0 to 50 wt. % of resin (B) and 25 to 80 wt. % of resin (C).

7. The porous polypropylene film according to Item 1 above, wherein the β-crystal nucleating agent is an amide compound represented by formula (1)

$$R^2\text{—NHCO—}R^1\text{—CONH—}R^3 \quad (1)$$

wherein $R^1$ is a $C_{1-24}$ saturated or unsaturated aliphatic dicarboxylic acid residue, a $C_{4-28}$ saturated or unsaturated alicyclic dicarboxylic acid residue, or a $C_{6-28}$ aromatic dicarboxylic acid residue, $R^2$ and $R^3$ are the same or different and each represents a $C_{3-18}$ cycloalkyl group, or a group of formula (a), formula (b), formula (c) or formula (d)

(a)

(b)

(c)

(d)

wherein $R^4$ is a hydrogen atom, a $C_{1-12}$ straight-chain or branched-chain alkyl group, a $C_{6-10}$ cycloalkyl group, or phenyl group, $R^5$ is a $C_{1-12}$ straight-chain or branched-chain alkyl group, and $R^6$ and $R^7$ are the same or different and each represents a $C_{1-4}$ straight-chain or branched-chain alkylene group.

8. A process for producing the porous polypropylene film with excellent breathability and continuous through-pores according to Item 1 above, the process being characterized in that it comprises stretching an unstretched web sheet made of a polypropylene-based resin composition comprising (I) (i) a propylene-ethylene copolymer having an ethylene content of 3.0 to 7.0 wt. % and a melt flow rate (MFR, JIS K-6857) measured at 230° C. of 2.0 to 4.0 g/10 min or (ii) a polypropylene-based resin mixture containing a propylene-ethylene copolymer and having an ethylene content of 3.0 to 7.0 wt. % and a melt flow rate (MFR, JIS K-6857) measured at 230° C. of 2.0 to 4.0 g/10 min and (II) a β-crystal nucleating agent; the unstretched web sheet having a thermally stable β-crystal (β1-crystal) content of 65% or higher and a β1-crystal heat of fusion per unit weight of the unstretched web sheet of 50 J/g or higher, as determined by differential scanning calorimetry (DSC).

9. The process for producing the porous polypropylene film according to Item 8 above, wherein the unstretched web sheet is made of a polypropylene-based resin composition comprising (I) a polypropylene-based resin mixture containing a propylene-ethylene copolymer and having an ethylene content of 3.0 to 7.0 wt. % and a melt flow rate (MFR, JIS K-6857) measured at 230° C. of 2.0 to 4.0 g/10 min, and (II) a β-crystal nucleating agent; and at least one component of the polypropylene-based resin mixture is a polypropylene-based resin having a weight average molecular weight (Mw) of $10^5$ to $10^6$ as determined by gel permeation chromatography (GPC) and a melt flow rate (MFR, JIS K-6857) measured at 230° C. of 0.5 to 10.0 g/10 min.

10. The process for producing the porous polypropylene film according to Item 8 above, wherein the unstretched web sheet is formed by cooling and solidifying in the form of a sheet, under the following crystallization conditions, a molten sheet of the polypropylene-based resin composition extruded from a T-die:

$$110° \text{ C.} < \text{crystallization temperature } (Tcr, ° \text{ C.}) \leq 130° \text{ C.}$$

Shortest crystallization holding time (tmin (sec))≦crystallization holding time (tcr, sec)<60 seconds wherein tmin (sec) is calculated by the following equations:

In the case of $Tcr<120° \text{ C.}$, $tmin(sec)=0.1(120-Tcr)^2+10$

In the case of $Tcr\geq120° \text{ C.}$, $tmin(sec)=0.3(120-Tcr)^2+10$.

11. The process for producing the porous polypropylene film according to Item 10 above, wherein the crystallization holding time condition is satisfied by crystallizing the molten sheet of the polypropylene-based resin composition extruded from a T-die, using a multistage chill roll having a plurality of chill-rolls or using one chill-roll in combination with other heat source.

12. The process for producing the porous polypropylene film according to Item 8 above, wherein the stretching is a successive biaxial stretching.

13. The process for producing the porous polypropylene film according to Item 12 above, characterized in that the successive biaxial stretching is carried out by conducting machine direction stretching at a ratio of 4 to 5 times at a stretching temperature of 70 to 90° C. and then transverse direction stretching at a ratio of 5 to 10 times at a stretching temperature of 135 to 155° C. and at a stretching rate of 10 to 300%/sec.

14. A backsheet for absorbent articles, characterized in that it comprises the porous polypropylene film with excellent breathability and continuous through-pores according to any one of Items 1 through 7 above.

15. An absorbent article comprising a liquid-permeable topside material, a fluid-impervious backside material and an absorbing material interposed between the topside material and the backside material, wherein the backsheet comprising the porous polypropylene film according to Item 14 above is employed as the backside material.

16. The absorbent article according to Item 15 above, which is a hygienic article such as a disposable diaper, pants-shaped diaper, sanitary napkin, incontinence pad and the like.

In this specification, the term "β1-crystal content" means the proportion of thermally stable β crystals (that is, β1 crystal) relative to the total amount of all crystals (that is, the sum of the amount of α crystals, β1 crystals and β2 crystals), as determined by differential scanning calorimetry (DSC). Also, the term "β1-crystal heat of fusion" denotes the β1-crystal heat of fusion per unit weight of an unstretched web sheet (that is, whole resin composition=crystal portion+ non-crystal portion).

DETAILED DESCRIPTION OF THE INVENTION

Polypropylene-Based Resin

The polypropylene-based resin used for producing a porous polypropylene film of the present invention is (i) a propylene-ethylene copolymer, or preferably (ii) a polypropylene-based resin mixture containing a propylene-ethylene block copolymer, and when using either (i) or (ii), the polypropylene-based resin is characterized by having an ethylene content of 3.0 to 7.0 wt. %, and preferably 4.0 to 5.0 wt. %, and an MFR of 2.0 to 4.0 g/10 min.

Specifically, in the present invention, (i) a propylene-ethylene copolymer having an ethylene content of 3.0 to 7.0 wt. % and a melt flow rate (MFR, JIS K-6857) measured at 230° C. of 2.0 to 4.0 g/10 min is used alone, or (ii) a polypropylene-based resin mixture containing a propylene-ethylene copolymer and having an ethylene content of 3.0 to 7.0 wt. % and a melt flow rate (MFR, JIS K-6857) measured at 230° C. of 2.0 to 4.0 g/10 min is used.

Hereinafter, the term "MFR" denotes a melt flow rate (JIS K-6857) measured at 230° C. unless specifically stated otherwise.

When the above-mentioned propylene-ethylene copolymer under item (i) above is used alone, the copolymer can be a random copolymer or a block copolymer, but preferably is a block copolymer.

When the above-mentioned polypropylene-based resin mixture under item (ii) above is used, it is sufficient that at least one component of the mixture is a propylene-ethylene copolymer. Thus, the mixture may be a mixture of two or more kinds of propylene-ethylene copolymers, or a mixture of at least one propylene-ethylene copolymer and other propylene-based resin(s). Again, the propylene-ethylene copolymer may be a random copolymer or a block copolymer, but preferably is a block copolymer.

There are no particular restrictions on the MFR, the ethylene content, or the content of each resin which is a component of the polypropylene-based resin mixture under item (ii) for use in the present invention, and they may be any values insofar as the polypropylene-based resin mixture has an ethylene content of 3.0 to 7.0 wt. % and an MFR of 2.0 to 4.0 g/10 min.

Generally, however, the propylene-ethylene copolymer used as one of the components of the above-mentioned polypropylene-based resin mixture under item (ii) above preferably contains about 70 to 99 wt. %, particularly 80 to 98 wt. %, of propylene and about 1 to 30 wt. %, particularly 2 to 20 wt. %, of ethylene.

Examples of the above-mentioned other propylene-based resin(s) are polymers mainly comprising propylene, specifically propylene homopolymers, copolymers of a) propylene and b) at least one comonomer selected from the group consisting of ethylene and $C_{4-8}$ 1-alkenes (including random copolymers and block copolymers) and the like (but excluding propylene-ethylene copolymers). Such copolymers preferably contain about 70 to 99 wt. %, particularly 80 to 98 wt. %, of propylene. The above-mentioned 1-alkenes include 1-butene, 1-pentene, 1-hexene, 1-peptene, 1-octene and the like. Moreover, the above-mentioned other propylene-based resin may contain a small amount of polyethylene or ethylene-propylene rubber.

In this specification, the above-mentioned propylene-ethylene copolymers and said other propylene-based resins are sometimes collectively referred to as "polypropylene-based resin".

When the MFR of the propylene-ethylene copolymer used alone or the MFR of the polypropylene-based resin mixture exceeds 4.0 g/10 min, the resulting film shows a strong tendency to break during stretching. When the MFR thereof is less than 2.0 g/10 min, the resulting film will have very low air permeability.

When the ethylene content of the propylene-ethylene copolymer used alone or the ethylene content of the polypropylene-based resin mixture exceeds 7.0 wt. %, the resulting film shows a tendency to break during stretching. When the ethylene content thereof is less than 3.0 wt. %, uneven stretching is likely to occur in the stretching step, and moreover, the resulting film tends to have very low breathability.

Herein, the term "ethylene content" means the amount of ethylene in a propylene-ethylene copolymer when the above-mentioned propylene-ethylene copolymer under item (i) is used alone, or the total amount of ethylene (the total amount of ethylene-derived structural portions) contained in the above-mentioned polypropylene-based resin (for example, propylene-ethylene block copolymers, propylene-ethylene random copolymers, the above-mentioned other propylene-based resins, or polyethylene or ethylene-propylene rubber which may be contained therein in a small amount and so forth) when the above-mentioned propylene-based resin mixture containing a propylene-ethylene copolymer under item (ii) is used.

The above-mentioned ethylene content can generally be measured by the infrared spectrum method (J. Polym. Sci., 7, 203 (1964)).

When the polypropylene-based resin mixture under item (ii) above is used, it is recommended that at least one component, particularly all components, preferably be polypropylene-based resins having a weight average molecular weight (Mw) of $10^5$ to $10^6$ as determined by gel permeation chromatography (GPC) and an MFR of 0.5 to 10.0 g/10 min.

Furthermore, it is recommended that the above-mentioned polypropylene-based resin mixture under item (ii) be a resin mixture of at least two members of polypropylene-based resins selected from the following resins (A), (B) and (C):

(A) a polypropylene-based resin having an MFR of not less than 0.1 g/10 min and not more than 2.0 g/10 min, and preferably 0.5 to 1.0 g/10 min;
(B) a polypropylene-based resin having an MFR of more than 2.0 g/10 min and less than 4.0 g/10 min; and
(C) a polypropylene-based resin having an MFR of 4.0 to 10.0 g/10 min, and preferably 5.0 to 8.0 g/10 min.

The above-mentioned resins (A), (B) and (C) are polymers which mainly comprise propylene, and specifically include propylene homopolymers, copolymers of a) propylene and b) at least one comonomer selected from the group consisting of ethylene and $C_{4-8}$ 1-alkenes (including random copolymers and block copolymers), and the like. The copolymers include those mainly comprising propylene, preferably those containing 70 to 99 wt. %, and more preferably 80 to 98 wt. %, of propylene. The above-mentioned 1-alkenes include 1-butene, 1-pentene, 1-hexene, 1-peptene, 1-octene and the like.

Although the details are not clarified, among resins (A), (B) and (C) constituting the above-mentioned resin mixture, resin (A) mainly acts to effectively reduce the breakage of films mainly during stretching. Resin (C) seems to mainly promote the formation of continuous through-pores. Also, the physical properties of resin (B) are positioned between those of resins (A) and (C), and resin (B) is preferably used for adjusting the balance of the whole mixture.

In the present invention, it is particularly preferable to use all three of the resins, i.e., resins (A), (B) and (C), or two of the resins, i.e., resins (A) and (C).

The proportions of resins (A), (B) and (C) are not specifically restricted insofar as resins (A), (B) and (C) can respectively exhibit the effect of resin (A) of reducing the breakage of films, the effect of resin (C) of promoting the formation of continuous through-pores, and the effect of resin (B) of adjusting the balance of the whole mixture, but preferably it is recommended to select the proportions from the following range: (A) 10 to 35 wt. %, (B) 0 to 50 wt. %, and (C) 25 to 80 wt. %, percentages of (A),(B) and (C) adding up to 100%. Moreover, it is more preferable that when the amount of (B) is in the range of 0 to 10 wt. %, the amount of (A) is in the range of 20 to 35 wt. % and the amount of (C) is in the range of 65 to 80 wt. %, and that when the amount of (B) is in the range of 10 to 50 wt. %, the amount of (A) is in the range of 10 to 25 wt. % and the amount of resin (C) is in the range of 25 to 75 wt. %. Resins (A), (B) and (C) each need not consist of only one resin, and at least one of resins (A), (B) and (C) may be a mixture of two or more components.

In any of the above-mentioned cases, resins (A), (B) and (C) are selected to satisfy the following three requirements: 1) at least one component is a propylene-ethylene copolymer; 2) the ethylene content of a mixture of at least two members selected from resins (A), (B) and (C) is 3.0 to 7.0 wt. %, preferably 4.0 to 5.0 wt. %; and 3) the MFR of the mixture of at least two members selected from resins (A), (B) and (C) is 2.0 to 4.0 g/10 min.

The above-mentioned resins (A), (B) and (C) each are preferably a propylene-ethylene copolymer or propylene homopolymer having a weight average molecular weight (Mw) of $10^5$ to $10^6$.

There are no particular restrictions on a method for mixing two or more kinds of resins, especially a method for mixing at least two members selected from the above-mentioned resins (A), (B) and (C), insofar as each resin can exhibit the aforementioned effect. Examples of such methods include a method in which the mixture is prepared during propylene polymerization, a method in which resins that have each been separately polymerized are mixed, and so forth. However, from an industrial viewpoint, as compared with the polymerization method that gives a multi-stage molecular weight distributions, simpler and preferable is the method in which the resins, especially resins (A), (B) and (C), each separately prepared by polymerization, are mixed optionally with the addition of a β-nucleating agent. The method for mixing at least two members of resins which have each been separately prepared by polymerization optionally with the addition of a β-nucleating agent can include any conventional method used for uniformly mixing two kinds of resins. For example, such mixing process can be carried out by dry-blending the resins in a known mixing apparatus, such as a Henschel mixer, a ribbon blender, a Banbury mixer or the like, and then melt-kneading the resulting blend in a single or double screw extruder.

The polymerization method for the polypropylene-based resin for use in the present invention includes not only a method which employs a generally used Ziegler-Natta type catalyst system, but also any method which employs a catalyst system comprising an alkylaluminum compound (triethylaluminum, diethylaluminum chloride or the like) in combination with a catalyst prepared by supporting a transition metal compound (for example, a titanium halide, such as titanium trichloride, titanium tetrachloride or the like) on a support mainly composed of magnesium halide, such as magnesium chloride or the like, or a metallocene catalyst system, etc. The stereospecificity of the resulting polymer can be either isotactic or syndiotactic.

β-Crystal Nucleating Agent

The β-crystal nucleating agent for use in the present invention is not particularly restricted, and includes a wide variety of conventionally used β-crystal nucleating agents. Examples of β-crystal nucleating agents generally include alkali metal or alkaline earth metal salts of carboxylic acid, such as potassium 1,2-hydroxystearate, magnesium benzoate, magnesium succinate, magnesium phthalate, etc.; aromatic sulfonic acid compounds, such as sodium benzenesulfonate, sodium naphthalenesulfonate, etc.; diesters and triesters of dibasic or tribasic carboxylic acids; tetraoxaspiro compounds; imido-carboxylic acid derivatives; pigments, such as phthalocyanine blue or other phthalocyanine-based pigments, and quinacridon, quinacridonquinone and other quinacridon-based pigments; binary system composed of component A, which is an organic dibasic acid, and component B, which is an oxide, a hydroxide or a salt of a metal of the group IIA in the periodic table; amide compounds represented by the following formulas (1) to (3) and the like. Among the above examples, amide compounds of the formula (1) are preferable, since they have no problem of coloration and so forth, and are most suitable in forming β1-crystals, which are thermally stable β-crystals.

$$R^2\text{—NHCO—}R^1\text{—CONH—}R^3 \tag{1}$$

wherein $R^1$ is a $C_{1-24}$ saturated or unsaturated aliphatic dicarboxylic acid residue, a $C_{4-28}$ saturated or unsaturated alicyclic dicarboxylic acid residue, or a $C_{6-28}$ aromatic dicarboxylic acid residue, $R^2$ and $R^3$ are the same or different and each represents a $C_{3-18}$ cycloalkyl group or a group of formula (a), formula (b), formula (c) or formula (d)

(a)

(b)

(c)

(d)

wherein $R^4$ is a hydrogen atom, a $C_{1-12}$ straight-chain or branched-chain alkyl group, a $C_{6-10}$ cycloalkyl group, or phenyl group, $R^5$ is a $C_{1-12}$ straight-chain or branched-chain alkyl group, and $R^6$ and $R^7$ are the same or different and each represents a $C_{1-4}$ straight-chain or branched-chain alkylene group.

$$R^9\text{—CONH—}R^8\text{—NHCO—}R^{10} \tag{2}$$

wherein $R^8$ is a $C_{1-24}$ saturated or unsaturated aliphatic diamine residue, a $C_{4-28}$ alicyclic diamine residue, a $C_{6-12}$ heterocyclic diamine residue or a $C_{6-28}$ aromatic diamine residue, $R^9$ and $R^{10}$ are the same or different and each represents a $C_{3-12}$ cycloalkyl group or a group of formula (e), formula (f), formula (g) or formula (h)

(e)

(f)

(g)

(h)

wherein $R^{11}$ is a hydrogen atom, a $C_{1-12}$ straight-chain or branched-chain alkyl group, a $C_{6-10}$ cycloalkyl group, or phenyl group, $R^{12}$ is a $C_{1-12}$ straight-chain or branched-chain alkyl group, a $C_{6-10}$ cycloalkyl group, or phenyl group, and $R^{13}$ and $R^{14}$ are the same or different and each represents a $C_{1-4}$ straight-chain or branched-chain alkylene group.

$$R^{16}\text{—CONH—}R^{15}\text{—CONH—}R^{17} \tag{3}$$

wherein $R^{15}$ is a $C_{1-28}$ saturated or unsaturated aliphatic amino acid residue, a $C_{6-12}$ saturated or unsaturated alicyclic amino acid residue or a $C_{6-14}$ aromatic amino acid residue, $R^{16}$ has the same meaning as $R^2$ or $R^3$ in formula (1), and $R^{17}$ has the same meaning as $R^9$ or $R^{10}$ in formula (2).

In the above-mentioned formula (1), the term "dicarboxylic acid residue" denotes a residue (divalent group) obtained by removing two carboxyl groups from a dicarboxylic acid. Also, in the above-mentioned formula (2), the term "diamine residue" means a residue (divalent group) obtained by removing two amino groups from a diamine. In the above-mentioned formula (3), "amino acid residue" denotes a residue (divalent group) obtained by removing one carboxyl group and one amino group from an amino acid.

The amide compounds of the above-mentioned formulas (1), (2) and (3) are generally known compounds, and can be easily produced by known methods.

The amide compounds of formula (1) can be easily prepared by subjecting an aliphatic, alicyclic or aromatic dicarboxylic acid represented by formula (1a)

$$HOOC-R^{18}-COOH \qquad (1a)$$

wherein $R^{18}$ has the same meaning as $R^1$ above, and one or two kinds of alicyclic or aromatic monoamines represented by formula (1b)

$$R^{19}-NH_2 \qquad (1b)$$

wherein $R^{19}$ has the same meaning as $R^2$ or $R^3$ above to amidation according to conventional methods.

Thus, "dicarboxylic acid residue" represented by $R^1$ in formula (1) refers to a residue (divalent group) obtained by removing two carboxyl groups from the following aliphatic, alicyclic or aromatic dicarboxylic acid. Also, $R^2$ and $R^3$ in formula (1) each represent a residue obtained by removing an amino group from the alicyclic or aromatic amine mentioned later.

Examples of aliphatic dicarboxylic acids include $C_{3-26}$, preferably $C_{3-14}$, saturated or unsaturated aliphatic dicarboxylic acids. Specific examples include malonic acid, diphenyl malonic acid, succinic acid, phenylsuccinic acid, diphenylsuccinic acid, glutaric acid, 3,3-dimethylglutaric acid, adipic acid, pimelic acid, suberic acid, azelaic acid, sebacic acid, 1,12-dodecanedioic acid, 1,14-tetradecanedioic acid and 1,18-octadecanedioic acid.

Examples of alicyclic dicarboxylic acids include $C_{6-30}$, preferably $C_{8-12}$, alicyclic dicarboxylic acids. Specific examples include 1,2-cyclohexanedicarboxylic acid, 1,4-cyclohexanedicarboxylic acid and 1,4-cyclohexane-diacetic acid.

Examples of aromatic dicarboxylic acids include $C_{8-30}$, preferably $C_{8-22}$, aromatic dicarboxylic acids, and specifically include p-phenylenediacetic acid, p-phenylenediethanoic acid, phthalic acid, 4-tert-butylphthalic acid, isophthalic acid, 5-tert-butyl-isophthalic acid, terephthalic acid, 1,8-naphthalic acid, 1,4-naphthalenedicarboxylic acid, 2,6-naphthalenedicarboxylic acid, 2,7-naphthalenedicarboxylic acid, diphenic acid, 3,3'-biphenyldicarboxylic acid, 4,4'-biphenyldicarboxylic acid, 4,4'-binaphthyldicarboxylic acid, bis(3-carboxyphenyl)methane, bis(4-carboxyphenyl)methane, 2,2-bis(3-carboxyphenyl)propane, 2,2-bis(4-carboxyphenyl)propane, 3,3'-sulfonyldibenzoic acid, 4,4'-sulfonyldibenzoic acid, 3,3'-oxydibenzoic acid, 4,4'-oxydibenzoic acid, 3,3'-carbonyldibenzoic acid, 4,4'-carbonyldibenzoic acid, 3,3'-thiodibenzoic acid, 4,4'-thiodibenzoic acid, 4,4'-(p-phenylenedioxy)dibenzoic acid, 4,4'-isophthaloyldibenzoic acid, 4,4'-terephthaloyldibenzoic acid, dithiosalicylic acid, and other such aromatic dicarboxylic acids.

Examples of alicyclic monoamines include $C_{3-18}$ cycloalkylamines and compounds represented by formula (4)

wherein $R^{20}$ has the same meaning as $R^5$ above, or compounds represented by formula (5)

wherein $R^{21}$ has the same meaning as $R^7$ above.

Specific examples include cyclopropylamine, cyclobutylamine, cyclopentylamine, cyclohexylamine, 2-methyloyclohexylamine, 3-methylcyclohexylamine, 4-methylcyclohexylamine, 2-ethylcyclohexylamine, 4-ethylcyclohexylamine, 2-propylcyclohexylamine, 2-isopropylcyclohexylamine, 4-propylcyclohexylamine, 4-isopropylcyclohexylamine, 2-tert-butylcyclohexylamine, 4-n-butylcyclohexylamine, 4-isobutylcyclohexylamine, 4-sec-butylcyclohexylamine, 4-tert-butylcyclohexylamine, 4-n-amyloyclohexylamine, 4-isoamylcyclohexylamine, 4-sec-amylcyclohexylamine, 4-tert-amyloyclohexylamine, 4-hexylcyclohexylamine, 4-heptylcyclohexylamine, 4-octylcyclohexylamine, 4-nonylcyclohexylamine, 4-decylcyclohexylamine, 4-undecylcyclohexylamine, 4-dodecylcyclohexylamine, 4-cyclohexylcyclohexylamine, 4-phenylcyclohexylamine, cycloheptylamine, cyclododecylamine, cyclohexylmethylamine, α-cyclohexylethylamine, β-cyclohexylethylamine, α-cyclohexylpropylamine, β-cyclohexylpropylamine and γ-cyclohexylpropylamine.

Examples of aromatic monoamines include compounds represented by formula (6)

wherein $R^{22}$ has the same meaning as $R^4$ above, or compounds represented by formula (7)

wherein $R^{23}$ has the same meaning as $R^6$ above.

Specific examples include aniline, o-toluidine, m-toluidine, p-toluidine, o-ethylaniline, p-ethylaniline, o-propylaniline, m-propylaniline, p-propylaniline, o-cumidine, m-cumidine, p-cumidine, o-tert-butylaniline, p-n-butylaniline, p-isobutylaniline, p-sec-butylaniline, p-tert-butylaniline, p-n-amylaniline, p-isoamylaniline, p-sec-amylaniline, p-tert-amylaniline, p-hexylaniline, p-heptylaniline, p-octylaniline, p-nonylaniline, p-decylaniline, p-undecylaniline, p-dodecylaniline, p-cyclohexylaniline, o-aminodiphenyl, m-aminodiphenyl, p-aminodiphenyl, benzylamine, α-phenylethylamine, β-phenylethylamine, α-phenylpropylamine, β-phenylpropylamine and γ-phenylpropylamine.

Of the compounds represented by formula (1), examples of favorable compounds include compounds wherein $R^1$ is a $C_{1-12}$ saturated or unsaturated aliphatic dicarboxylic acid residue, a $C_{6-10}$ saturated or unsaturated alicyclic dicarboxylic acid residue or a $C_{6-20}$ aromatic dicarboxylic acid residue, and $R^2$ and $R^3$ are the same or different and each represents a $C_{3-12}$ cycloalkyl group or a group represented by formula (a), formula (b), formula (c) or formula (d).

Among these compounds, more preferable compounds include compounds represented by formula (1) wherein $R^1$ is a $C_{4-8}$ saturated aliphatic dicarboxylic acid residue, a $C_{6-8}$ saturated alicyclic dicarboxylic acid residue or a $C_{6-12}$ aromatic dicarboxylic acid residue, and $R^2$ and $R^3$ each represent a $C_{4-8}$ cycloalkyl group or phenyl group.

Among the amide compounds represented by formula (1), particularly preferable compounds include N,N'-dicyclohexyl-2,6-naphthalenedicarboxamide.

It is recommended that the amide compounds for use in the present invention have a maximum particle diameter of not more than 20 µm, preferably not more than 10 µm, and more preferably not more than 5 µm. A maximum particle diameter exceeding 20 µm may lead to the breakage of the resulting film during stretching. The maximum particle diameter denotes a particle diameter as measured using laser diffraction analysis.

It is recommended that the amount of β-crystal nucleating agent to be used in the present invention be 0.0001 to 5 weight parts, and preferably 0.001 to 1 weight part, per 100 weight parts of the above-mentioned propylene-ethylene copolymer under item (i) or the polypropylene-based resin mixture under item (ii). If the amount of β-crystal nucleating agent is less than 0.0001 weight part, β1 crystals tend not to be produced in sufficient quantity, which leads to a reduction in permeability of the resulting film. On the other hand, even if the amount exceeds 5 weight parts, no marked improvement in effect is observed, and furthermore, breakage may be caused in the stretching step, which is not desirable.

The β-nucleating agent can be mixed when preparing a polypropylene-based resin or can be added when mixing resins that have been prepared separately. The method for mixing the β-nucleating agent with the resin includes known methods used for mixing a polypropylene resin and an additive.

Porous Polypropylene-Based Resin Film

A porous polypropylene film of the present invention is a film made of the above-mentioned polypropylene-based resin composition and having continuous through-pores, and has the following characteristics:

(1) porosity is in the range of 20 to 80%;
(2) Gurley air permeability measured according to JIS P-8117 (hereinafter simply referred to as "Gurley air permeability") is 5,000 sec/100 cc or lower;
(3) water vapor permeability measured according to JIS Z-0208 (hereinafter simply referred to as "water vapor permeability") is 2,000 g/m²·24 h or higher;
(4) water pressure resistance measured according to JIS L-1092 except that a 0.25 wt. % aqueous solution of a surfactant (sodium polyoxyethylene (3) lauryl ether sulfate) is used instead of pure water (hereinafter referred to simply as "water pressure resistance") is 75 kPa or higher.

These characteristics are illustrated below.

From the viewpoint of an absorbent article produced using a porous film of the present invention as a backsheet being comfortable to wear without causing a stuffy feeling, the porous film of the present invention has a Gurley air permeability of not more than 5,000 sec/100 cc, preferably not more than 1,500 sec/100 cc, and a water vapor permeability of not less than 2,000 g/m²·24 h, preferably not less than 3,000 g/m²·24 h. The minimum value of the Gurley air permeability is not specifically restricted, but about 10 sec/100 cc is preferable, and about 100 sec/100 cc is more preferable. The maximum value of the water vapor permeability is not specifically restricted, but about 20,000 g/m²·24 h, and about 10,000 g/m²·24 h is more preferable.

If the Gurley air permeability is 10 sec/100 cc or lower, or the water vapor permeability exceeds 20,000 g/m²·24 h, the water pressure resistance and tensile strength are lowered, and it becomes difficult to obtain the desired characteristics of the present invention.

The water pressure resistance of a porous film used as a backside material of a conventional diaper for infants is about 15 kPa as measured by the same methods as mentioned above (the methods described in the Examples of this invention). On the contrary, the water pressure resistance of the porous film of the present invention is at least 5 times as high as that of a conventional film, that is, 75 kPa or higher, and preferably 10 times, that is, 150 kPa or higher, so it can be used for diapers for adults without uneasiness about urinary incontinence. The maximum value of the water pressure resistance is not specifically restricted, but from a viewpoint of making it easy to obtain the desired Gurley air permeability and water vapor permeability, the maximum water pressure resistance is preferably about 400 kPa, and more preferably about 300 kPa.

While the thickness of the porous polypropylene film of the present invention can be adjusted appropriately based on the requirement of its use, by changing the thickness of the unstretched web sheet and the area stretch ratio, it is recommended that the thickness of the porous polypropylene film be 5 to 50 µm, preferably 8 to 20 µm when breathability, texture, mechanical strength and leakage prevention are taken into consideration. When the thickness is below 5 µm, it tends to be difficult to obtain sufficient mechanical strength and leakage prevention, and when the thickness exceeds 50 µm, it tends to be difficult to obtain sufficient breathability and good texture.

Moreover, it has been found that in order to prevent the backside material from tearing when attaching or detaching a closure tape, it needs to have a tensile strength in its weakest direction of 200 kgf or higher, preferably 300 kgf or higher, per cm of film width. The porous film of the present invention, when having a thickness of 5 to 50 µm, has a tensile strength (mechanical strength measured according to JIS K-7127) of 40 MPa or higher, particularly 60 MPa or higher, and therefore is preferable from the viewpoint of strength as well.

The porous film of the present invention has the above-mentioned breathability, water vapor permeability and leakage prevention, and moreover, has a porosity of 20 to 80%, and preferably 30 to 60%. Film having a porosity of less than 20% cannot have Gurley air permeability and water vapor permeability within the above-mentioned range, and film having a porosity of more than 80% cannot achieve water pressure resistance within the above-mentioned range.

The porous polypropylene film of the present invention is not only excellent in breathability and water vapor permeability, but also excellent in leakage prevention and mechanical strength. Accordingly, the film of the present invention can be widely used in the fields of light rainwear, light work clothes and other moisture-permeable waterproof garments; paper diapers, sanitary products and other such absorbent articles; bed sheets and other hygienic merchandise; waterproof sheets, wallpaper and other construction materials; packaging materials for desiccants, deoxygenators, chemical hand warmers and the like; synthetic paper, filtration membranes and separation membranes, battery separators used in batteries and in electrolysis and the like; medical materials; agricultural multi-sheets; and so forth.

Among the above-mentioned products, an absorbent article using the porous polypropylene-based film of the present invention as a backsheet has sufficient strength, and thus the backside material of the article will not break when attaching or detaching a closure tape. Moreover, the absorbent article is excellent in leakage prevention, and there is no need for concern about urinary incontinence when used as diapers for adults, and thus the article can be used comfortably. Furthermore, the absorbent article has excellent breathability, water vapor permeability and good texture and is comfortable to wear without causing a stuffy feeling.

Process for Producing a Porous Polypropylene-Based Resin Film

The porous polypropylene-based resin film of the present invention having the above-mentioned characteristics can be prepared, for example, by producing an unstretched web sheet from a resin composition containing the above-mentioned polypropylene-based resin and the above-mentioned β-nucleating agent, and stretching the resulting unstretched web sheet.

That is, the process for producing the porous polypropylene film of the present invention with excellent breathability and continuous through-pores is characterized by stretching an unstretched web sheet composed of a polypropylene-based resin composition comprising:

(I) (i) a propylene-ethylene copolymer having an ethylene content of 3.0 to 7.0 wt. % and a melt flow rate (MFR, JIS K-6857) measured at 230° C. of 2.0 to 4.0 g/10 min, or
  (ii) a polypropylene-based resin mixture containing a propylene-ethylene copolymer, the mixture having an ethylene content of 3.0 to 7.0 wt. % and a melt flow rate (MFR, JIS K-6857) measured at 230° C. of 2.0 to 4.0 g/10 min, and
(II) a β-crystal nucleating agent, wherein the proportion of thermally stable β crystals (β1 crystals) relative to the total amount of all crystals is 65% or higher and the β1-crystal heat of fusion is 50 J/g or higher, as determined by differential scanning calorimetry (DSC).

Hereinafter, (AA) an unstretched web sheet and (BB) a process for producing the unstretched web sheet, and then (CC) a process for producing a porous polypropylene-based resin film of the present invention are described.

(AA) Unstretched Web Sheet

As mentioned above, the unstretched web sheet for use in the present invention is an unstretched web sheet composed of a polypropylene-based resin composition containing (I) (i) a propylene-ethylene copolymer having an ethylene content of 3.0 to 7.0 wt. % and a melt flow rate (MFR, JIS K-6857) measured at 230° C. of 2.0 to 4.0 g/10 min or (ii) a polypropylene-based resin mixture containing a propylene-ethylene copolymer, the mixture having an ethylene content of 3.0 to 7.0 wt. % and a melt flow rate (MFR, JIS K-6857) measured at 230° C. of 2.0 to 4.0 g/10 min; and
(II) a β-crystal nucleating agent.

In the present invention, it is recommended that the unstretched web sheet have the following physical properties. Specifically, it is recommended that DSC shows that 1) the β1-crystal content, i.e., the proportion of thermally stable β crystals (β1 crystals) relative to the total amount of all crystals (i.e., the sum of the amounts of α crystals, β1 crystals and β2 crystals), be at least 65%, preferably at least 70%, and more preferably at least 75%, and 2) the β1-crystal heat of fusion per unit weight of the unstretched web sheet (i.e., whole resin composition=crystal portion+non-crystal portion) be 50 J/g or higher, preferably 55 J/g or higher, more preferably 60 J/g or higher. When the β1-crystal content and the β1-crystal heat of fusion are within the above respective ranges, almost no independent pores are formed and a porous film having the desired properties can be easily obtained.

In the present invention, the β1-crystal content and the β1-crystal heat of fusion are determined by cutting an unstretched polypropylene sheet to a suitable size to prepare a sample, subjecting this sample to differential scanning calorimetry (DSC) in a nitrogen atmosphere and at a heating rate of 20° C./min, and then calculating the β1-crystal content and the β1-crystal heat of fusion according to the following equation using α-crystal and β1-crystal heat of fusion obtained from this DSC thermogram:

β1-crystal content(%)=100×(the β-crystal heat of fusion)/(sum of the α-crystal heat of fusion and the β-crystal heat of fusion)

The β1-crystal heat of fusion (J/g)=(the β-crystal heat of fusion)(J)/(the weight of unstretched web sheet sample) (g).

Since the β2 crystal, which is a metastable crystal, has lower heat stability than the β1 crystal, and almost all of the β2 crystals transform to α crystals by the heat given to the sample during DSC measurement, the β1-crystal content and the β1-crystal heat of fusion can be estimated from the DSC thermogram.

(BB) Process for Producing the Unstretched Web Sheet

In the present invention, the polypropylene-based resin described in the foregoing item "Polypropylene-based resin" is mixed (preferably, mixed uniformly) with the β-crystal nucleating agent described in the foregoing item "β-crystal nucleating agent" by a conventional method to produce a polypropylene-based resin composition (raw compound), and then an unstretched web sheet is prepared from the thus obtained polypropylene-based resin composition.

The polypropylene-based resin composition (raw compound), used for preparing the unstretched web sheet of the present invention having the β1-crystal content and the β1-crystal heat of fusion within the above-mentioned ranges, preferably contains the above-mentioned β-crystal nucleating agent and at least two kinds of polypropylene-based resins, at least one of the resins, particularly all the resins, having a weight average molecular weight (Mw) determined by gel permeation chromatography (GPC) of $10^5$ to $10^6$ and an MFR of 0.5 to 10.0 g/10 min.

Specifically, the unstretched web sheet of the present invention is composed of a polypropylene-based resin composition comprising (I) a polypropylene-based resin mixture containing a propylene-ethylene copolymer, the mixture having an ethylene content of 3.0 to 7.0 wt. % and a melt flow rate (MFR, JIS K-6857) measured at 230° C. of 2.0 to 4.0 g/10 min, and (II) a β-crystal nucleating agent, wherein at least one component of the polypropylene-based resin mixture is preferably a polypropylene-based resin having a weight average molecular weight (Mw) of $10^5$ to $10^6$ as determined by gel permeation chromatography (GPC) and a melt flow rate (MFR, JIS K-6857) measured at 230° C. of 0.5 to 10.0 g/10 min.

More preferably, it is recommended that the polypropylene-based resin mixture used for the process of the present invention is a resin mixture comprising at least two resins selected from polypropylene-based resins represented by the above-mentioned (A), (B) and (C).

Conventional polyolefin modifiers can be appropriately added to the polypropylene-based resin composition according to the present invention as dictated by the intended use and application, to the extent that the effect of the present invention is not impaired.

Examples of such polyolefin modifiers include various additives described in the "Digest of Positive List of Additives" (October, 1990) edited by the Japan Hygienic Olefin And Styrene Plastics Association. Specific examples include stabilizers (such as metal compounds, epoxy compounds, nitrogen compounds, phosphorus compounds and sulfur compounds), UV absorbers (such as benzophenone compounds and benzotriazole compounds), antioxidants (such as phenol compounds, phosphorous ester compounds, and sulfur compounds), surfactants, lubricants (such as paraffin, wax and other aliphatic hydrocarbons, $C_{8-22}$ higher fatty acids, $C_{8-22}$ higher fatty acid metal (Al, Ca, Mg, Zn) salts, $C_{8-18}$ fatty acids, $C_{8-22}$ aliphatic alcohols, polyglycols, esters of $C_{4-22}$ higher fatty acids and $C_{4-18}$ aliphatic monohydric alcohols, $C_{8-22}$ higher fatty acid amides, silicone oils and rosin derivatives), fillers (such as talc, hydrotalcite, mica, zeolite, perlite, diatomaceous earth, calcium carbonate and glass fiber), foaming agents, foaming auxiliaries, polymer additives, plasticizers, crosslinking agents, crosslinking accelerater, antistatic agents, neutralizers, anti-blocking agents, anti-fogging agents, polymer alloy components (such as block SBR, random SBR, hydrogenated products thereof, and like rubbers, and polystyrenes), flame retardants, dispersants, organic and inorganic pigments and dyes, and working auxiliaries.

The processes for producing the unstretched web sheet of the present invention having the above-mentioned characteristics may include a variety of processes, but the processes such as mentioned below are preferable.

The preferable process comprises the steps of dry-blending the aforementioned (i)propylene-ethylene copolymer or (ii)polypropylene-based resin mixture with a β-crystal nucleating agent (and optionally the aforementioned one or more polyolefin modifiers) in a known mixer, such as a Henschel mixer, tumbler mixer, V blender, ribbon blender, Banbury mixer and the like, melt-kneading the resulting mixture in a single or double screw extruder or the like, and then cooling and palletizing the mixture to obtain a polypropylene-based resin composition (raw compound). The temperature in the mixing process generally ranges from room temperature to about 100° C. and the mixing time varies depending on the rotational speed of the device, but is generally about 1 to 20 minutes. Also, the temperature in the melt-kneading process is preferably 200 to 280° C.

Then, the obtained polypropylene-based resin composition pellets (raw compound) is extruded from an extruder equipped with a T-die or an inflation die to prepare a sheet, and cooling the sheet to obtain the desired unstretched web sheet.

Particularly, a molten sheet of polypropylene-based resin composition (raw compound) extruded from a T-die is preferably cooled and solidified under the following crystallization conditions (crystallization temperature, crystallization holding time).

The crystallization temperature as used herein is the temperature for cooling and solidifying a molten sheet, that is, the temperature of the sheet in the crystallization process. Specifically, when the molten sheet is cooled and solidified (crystallized) on a chill roll, the crystallization temperature corresponds to the surface temperature of the chill roll. Also, the crystallization holding time is the time during which the sheet is maintained at the above-mentioned crystallization temperature. Specifically, when the molten sheet is cooled and solidified (crystallized) on the chill roll, the time denotes the contact time between the sheet and the chill roll.

[Crystallization Temperature (Tcr, ° C.)]

$$110° C. < Tcr \leq 130° C.$$

Preferably, $115° C. \leq Tcr \leq 125° C.$

More preferably, $Tcr = 120 \pm 3° C.$

[Crystallization Holding Time (Tcr, sec)]

Shortest crystallization holding time (tmin (sec)) ≦ tcr < 60 seconds

Herein, the shortest crystallization holding time (tmin (sec)) is calculated by the following Equation 1 to Equation 4:

In the case of Tcr (° C.) < 120° C., $$tmin(sec) = 0.10(120 - Tcr)^2 + 10 \quad \text{(Equation 1)}$$

Preferably, $$tmin(sec) = 0.25(120 - Tcr)^2 + 20 \quad \text{(Equation 2)}$$

In the case of Tcr (° C.) ≧ 120° C., $$tmin(sec) = 0.30(120 - Tcr)^2 + 10 \quad \text{(Equation 3)}$$

Preferably, $$tmin(sec) = 0.40(120 - Tcr)^2 + 20 \quad \text{(Equation 4).}$$

When Tcr is 110° C. or lower, the desired β1-crystal content and the β1-crystal heat of fusion are not achieved, irrespective of the tcr value. When Tcr is higher than 130° C., the desired β1-crystal content and the β1-crystal heat of fusion are not achieved unless tcr is set to be at least 60 seconds or longer, and therefore productivity is significantly decreased.

The β1-crystal generation speed reaches the maximum at about 120° C., and the generation speed falls as the temperature deviates from 120° C. or so. Therefore, in the case of Tcr=120° C., the desired amount of β1-crystals are generated when tcr is at least 10 seconds, preferably at least 20 seconds. At temperatures other than 120° C., a tcr which is longer than tmin calculated by Equation 1 to Equation 4 is needed. For example, in the case of Tcr=130° C., tcr must be at least 40 seconds or longer to form the desired β1 crystals.

When tcr is set to be shorter than tmin calculated by Equation 1 to Equation 4, the desired β1-crystal content and the β1-crystal heat of fusion are not achieved, irrespective of the crystallization temperature. Moreover, when tcr is set to be longer than 60 seconds, the β1-crystal content and the β1-crystal heat of fusion can satisfy the desired range, but this reduces productivity and leads to a tremendous increase in production cost, and therefore is not desirable from an industrial viewpoint.

Industrially, it is necessary to increase productivity, i.e., molding speed, but taking equipment costs and the like into consideration, it is not practical to secure the above-mentioned tcr with used of only one chill roll. Thus, to increase the molding speed, it is practical and preferable to satisfy the above-mentioned crystallization holding time condition by crystallizing a molten sheet of a raw compound extruded from a T-die with use of a combination of a plurality of chill rolls, that is, with use of a multistage chill roll, or using one chill roll in combination with a heat source other than a chill roll. As the heat source other than a chill roll, a warm air heater, an IR heater, an oven, a hot bath or like temperature-holding equipment can be used either singly or in combination.

When the above-mentioned method is adopted, Tcr can be used as a single temperature or more than two temperatures, insofar as Tcr is within the above-mentioned range.

It is recommended that the molten resin temperature of the polypropylene-based resin composition (raw compound) extruded from a T-die should be in the range of 200 to 280° C. When the molten resin temperature is lower than 200° C., non-molten resin may be generated and breakage in the stretching step may occur. A molten resin temperature exceeding 280° C. leads to degradation of the resin, causing breakage in the stretching step and coloration of the resulting film. However, the molten state and degradation situation of the resin vary considerably with the type of the resin and the stabilizer used, and therefore it is not always required that the molten resin temperature be within the temperature range given above.

(CC) Process for Producing a Porous Polypropylene-Based Resin Film

A porous polypropylene film of the present invention, which has excellent breathability and continuous through-pores and is suitable for use as a backsheet for absorbent articles, can be produced by stretching the unstretched web sheet obtained above.

The stretching process can be carried out by any of uniaxial stretching and a simultaneous or successive-biaxial stretching, but a successive biaxial stretching method is specifically recommended.

In the case of the uniaxial stretching method or simultaneous biaxial stretching method, it is recommended that the stretching temperature be from 60 to 140° C., the stretch ratio in one direction be 4 to 8 times, and the area stretch ratio (machine direction stretch ratio×transverse direction stretch ratio) be 4 to 40 times.

In the case of the successive biaxial stretching method, it is desirable, as the machine direction stretching condition for the first step, that the stretching temperature be from 70 to 90° C. and that the stretch ratio be 4 to 5 times. A stretching temperature lower than 70° C. makes it difficult to stretch films uniformly, whereas a temperature exceeding 90° C. significantly lowers the breathability of the resulting film.

It is desirable, as the transverse direction stretching condition for the second step, that the stretching temperature be 135 to 155° C., preferably 140 to 150° C. and the stretch ratio be 5 to 10 times, preferably 7 to 8 times, and the stretching rate be 10 to 300%/sec, preferably 20 to 200%/sec, more preferably 40 to 150%/sec. A stretching temperature lower than 135° C. may lead to breakage during stretching, whereas a stretching temperature exceeding 155° C. significantly lowers the breathability of the resulting film. A stretch ratio lower than 5 times may lead to bad productivity, which is not economical, whereas a stretch ratio exceeding 8 times may lead to breakage during stretching.

The transverse direction stretching rate has an influence on the formation of continuous through-pores, and the slower the stretching rate is, the more easily it is to form the through-pores. If the stretching rate is slower than 300%/sec, continuous through-pores can be formed effectively, thus the porous film with excellent breathability of the present invention can be obtained advantageously, and moreover, breakage during stretching can be substantially avoided. If the stretching rate is slower than 10%/sec, the porous film of the present invention can be obtained, but it is desirable to carry out the stretching process at a stretching rate of not less than 10%/sec taking productivity into consideration from an industrial viewpoint.

The area stretch ratio (machine direction stretch ratio× transverse direction stretch ratio) can be adjusted appropriately by selecting the machine direction stretch ratio and transverse direction stretch ratio. The recommended area stretch ratio is 20 to 50 times, preferably 24 to 40 times, taking productivity and production stability into consideration.

A Backsheet and Absorbent Articles

As mentioned above, the porous polypropylene film of the present invention is excellent in not only breathability and water vapor permeability, but also leakage prevention and mechanical strength. Thus, the film of the present invention can be widely used in the fields of light rainwear, light work clothes and other moisture-permeable waterproof garments; hygienic articles (paper diapers (disposable diapers, pants-shaped diapers, etc.), sanitary napkins and other sanitary products, incontinence pads and absorbent articles, bed sheets and other hygienic merchandise); waterproof sheets, wallpaper and other construction materials; packaging materials for desiccants, deoxygenators, chemical hand warmers and the like; synthetic paper, filtration membranes and separation membranes, battery separators used in batteries and in electrolysis and the like; medical materials; agricultural multi-sheets; and so forth.

The porous polypropylene-based film of the present invention is especially suitable for use as a backsheet for the above-mentioned absorbent articles.

Thus, the present invention provides a backsheet for absorbent articles that comprises the porous polypropylene film of the present invention with excellent breathability and continuous through-pores.

Figure 1:
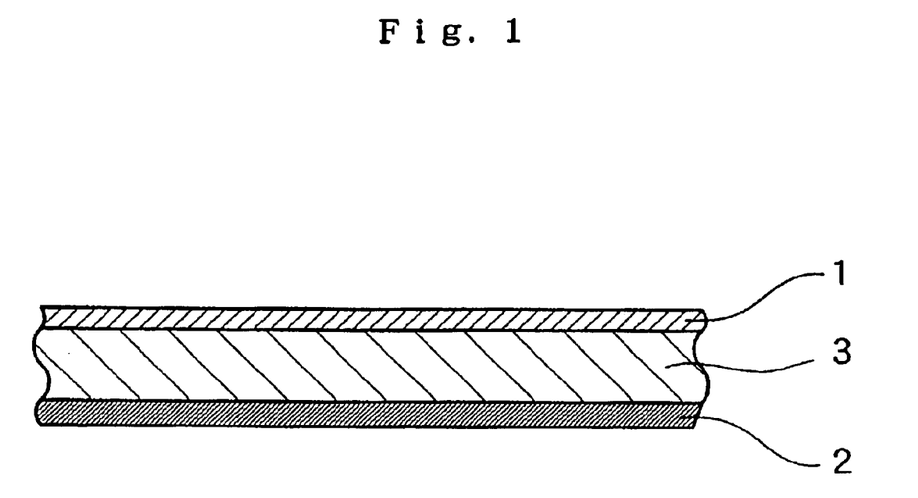
FIG. 1 is a cross-section diagram illustrating an absorbent article of the present invention.

Absorbent articles include articles having a structure as schematically outlined in FIG. 1.

Thus, the present invention also provides an absorbent article which comprises a liquid-permeable topside material 1, a leakage-prevention backside material 2 and an absorbing material 3 interposed between the topside material 1 and the backside material 2, wherein a backsheet composed of the above-mentioned porous polypropylene film of the invention is used as the backside material 2.

As the liquid-permeable topside material 1, various topside materials conventionally used in the field of such absorbent articles can be used. Preferable examples of such topside materials include non-woven fabrics made of polyethylene, polypropylene or like polyolefin, polyethylene sheets with pores and the like.

As the absorbing material 3, various absorbing materials conventionally used in the field of such absorbent articles can be used. Examples of such absorbing materials include fluffy pulp, absorbent paper, super-absorbent polymers such as starch-based or cellulose-based graft polymers, carboxymethylated polymers, polyacrylic acid salt-based polymers, polysulfonic acid salt-based polymers, polyvinyl alcohol-based polymers, polyvinyl alcohol/poly acrylic acid salt copolymer-based polymers, polyacrylamide-based polymers, polyoxymethylene-based polymers and like synthetic polymers. Generally, the above-mentioned superabsorbent polymers, fluffy pulp and absorbent paper are used as multilayered and/or as mixed.

The absorbent articles of the present invention can be easily produced by methods conventionally used in the art.

Absorbent articles include those in various forms as described in Fine Chemical, 24 (20), 16 (1995) and the like, and the backsheets and absorbent articles of the present invention can be used for absorbent articles in these various forms.

In the case of diapers and the like, it is naturally possible to provide an elastic function element which prevents excreta from leaking out beyond the waist or leg region, or a closure tape which fastens the diaper on the front and rear waist regions when wearing the diaper, and any known techniques which are adopted in the field of absorbent articles can be added.

Since an absorbent article prepared using the backsheet of the present invention has sufficient strength, the backside material of the article will not break when attaching or detaching a closure tape. Moreover, the article is excellent in leakage prevention, and there is no need for concern about urinary incontinence even when used in diapers for adults, and thus the article can be used comfortably. Furthermore, the absorbent article of the invention has excellent breathability, water vapor permeability and good texture and is comfortable to wear without causing a stuffy feeling.

EXAMPLES

The present invention will be illustrated in more detail with reference to the following examples and comparative examples. The ethylene content of a single resin or a resin mixture, the K value, the β1-crystal content, the β1-crystal heat of fusion of the unstretched web sheet, the porosity, Gurley air permeability, water vapor permeability, tensile strength and leakage prevention (water pressure resistance) of the stretched film were determined by the methods given below.

Ethylene content: A film having a thickness of about 50 μm was prepared using a compression molding machine, and the IR spectrum of the film was measured by the transmission technique with ten times averaging, using Parkin Elmer IR spectrometer 1720-X. The absorbance at 722 cm$^{-1}$, which is attributable to the ethylene unit, and the absorbance at 815 cm$^{-1}$, which is attributable to the propylene unit, were each read from the obtained IR spectrum, and the ethylene content (wt. %) was determined from the following equation.

$$\text{Ethylene content}=100 \times (a/1.2)/[(a/1.2)+(3b/0.6)]$$

wherein a is the absorbance at 722 cm$^{-1}$ and b is the absorbance at 815 cm$^{-1}$.

K value: An unstretched web sheet was subjected to X-ray diffraction, and the K value was determined from the following equation.

$$K \text{ value}=H(\beta_1)/[H(\beta_1)+H(\alpha_1)+H(\alpha_2)+H(\alpha_3)]$$

$H(\beta_1)$: diffraction intensity (height) of β-crystal (300) plane $H(\alpha_1)$: diffraction intensity (height) of α-crystal (110) plane $H(\alpha_2)$: diffraction intensity (height) of α-crystal (040) plane $H(\alpha_3)$: diffraction intensity (height) of α-crystal (130) plane β1-crystal content and β1-crystal heat of fusion: An unstretched polypropylene sheet was cut to a suitable size to prepare a sample, and this sample was subjected to differential scanning calorimetry (DSC) in a nitrogen atmosphere at a heating rate of 20° C./min using the Parkin Elmer DCS7. The β1-crystal content and the β1-crystal heat of fusion were each determined by the following equation using the α-crystal heat of fusion and β-crystal heat of fusion obtained from the DSC thermogram.

β1-crystal content (%)=100×(the β-crystal heat of fusion)/(sum of the α-crystal heat of fusion and the β-crystal heat of fusion)

β1-crystal heat of fusion (J/g)=the β-crystal heat of fusion (J)/sample weight (g)

Porosity: A stretched film was cut into a square and the length of one side (L cm), the weight (W g), and the thickness (D cm) were measured. The porosity was then calculated by the following equation:

$$\text{Porosity}=100-100(W/\rho)/(L^2 \times D)$$

wherein ρ is the density of the unstretched polypropylene film prior to stretching.

Gurley air permeability: Measured according to JIS P-8117.

Water vapor permeability: Measured according to JIS Z-0208.

Tensile strength: Measured according to JIS K-7127.

Leakage prevention: The water pressure resistance (kPa) was measured according to JIS L-1092 except that a 0.25 wt. % aqueous solution of a surfactant (sodium polyoxyethylene (3) lauryl ether sulfate) was used instead of pure water.

[Preparation of Raw Compound]

N,N'-Dicyclohexyl-2,6-naphthalenedicarboxamide (0.2 weight part, used as a β-crystal nucleating agent) and 0.05 weight part of Irganox 1010 and 0.05 weight part of Irgafos 168 (used as stabilizers) were mixed in a Henschel mixer with 100 weight parts of a polypropylene-based resin mixture having the composition shown in Table 1. This mixture was melt mixed at 240° C., and the extruded resin was cooled and pelletized. The MFR and ethylene content of the polypropylene-based resin mixture used are shown in Table 1.

The characteristics of each raw resin shown in table 1 are as follows:

A1: MFR=0.5 g/10 min, Mw=552,000, ethylene content=4.4 wt. % propylene-ethylene block copolymer A2: MFR=1.5 g/10 min, Mw=658,000, ethylene content=9.2 wt. % propylene-ethylene block copolymer A3: MFR=0.5 g/10 min, Mw=573,000, ethylene content=0.0 wt. % propylene homopolymer B1: MFR=2.5 g/10 min, Mw=512,000, ethylene content=4.7 wt. % propylene-ethylene block copolymer B2: MFR=2.9 g/10 min, Mw=385,000, ethylene content=0.0 wt. % propylene homopolymer C1: MFR=6.5 g/10 min, Mw=303,000, ethylene content=4.4 wt. % propylene-ethylene block copolymer C2: MFR=4.2 g/10 min, Mw=305,000, ethylene content=7.8 wt. % propylene-ethylene block copolymer.

Example 1

The raw compound PP1 was extruded in the form of a sheet at a resin temperature of 220° C. using a T-die extruder (twin screw extruder with a screw diameter of 65 mm, plus a T-die with a width of 350 mm). This sheet was cooled and solidified with use of a chill roll with a diameter of 600 mm and maintained at a surface temperature of 120° C., producing a polypropylene unstretched web sheet with a thickness of about 250 μm. The contact time (crystallization holding time) between the unstretched web sheet and the chill roll was 12 seconds. Next, the obtained unstretched web sheet was allowed to cool to room temperature, and the K value, β1-crystal content, and β1-crystal heat of fusion were measured. (These physical properties were measured after allowing the unstretched web sheet to cool to room temperature in the following examples and comparative examples as well.) The K value, β1-crystal content and β1-crystal heat of fusion of the unstretched web sheet are shown in Table 2.

The obtained unstretched web sheet was subjected to roll stretching in machine direction at a ratio of 4 times at a temperature of 80° C., and then subjected to tenter stretching in transverse direction at a ratio of 7.5 times and at 24%/sec and at 140° C., producing a white opaque stretched film. The thickness, porosity, Gurley air permeability, water vapor permeability, tensile strength and water pressure resistance of the obtained stretched film are shown in Table 2.

Example 2

A stretched film was prepared in the same manner as in Example 1 except that PP2 was used as the raw compound. The K value, β1-crystal content and β1-crystal heat of fusion of the obtained unstretched web sheet, and the thickness, porosity, Gurley air permeability, water vapor permeability, tensile strength and water pressure resistance of the stretched film are shown in Table 2.

Example 3

A stretched film was prepared in the same manner as in Example 1 except that PP3 was used as the raw compound, the machine direction stretching temperature was changed to 75° C., and the transverse direction stretching rate and stretch ratio were changed to 26%/sec and 8.0 times, respectively. The K value, β1-crystal content and β1-crystal heat of fusion of the obtained unstretched web sheet, and the thickness, porosity, Gurley air permeability, water vapor permeability, tensile strength and water pressure resistance of the stretched film are shown in Table 2.

Example 4

A stretched film was prepared in the same manner as in Example 1 except that PP4 was used as the raw compound, the machine direction stretching temperature was changed to 85° C., and the transverse direction stretching temperature, stretching rate and stretch ratio were changed to 145° C., 16%/sec and 5.0 times, respectively. The K value, β1-crystal content and β1-crystal heat of fusion of the obtained unstretched web sheet, and the thickness, porosity, Gurley air permeability, water vapor permeability, tensile strength and water pressure resistance of the stretched film are shown in Table 2.

Example 5

A stretched film was prepared in the same manner as in Example 1 except that PP5 was used as the raw compound. The K value, β1-crystal content and β1-crystal heat of fusion of the obtained unstretched web sheet, and the thickness, porosity, Gurley air permeability, water vapor permeability, tensile strength and water pressure resistance of the stretched film are shown in Table 2.

Example 6

A stretched film was prepared in the same manner as in Example 1 except that PP6 was used as the raw compound. The K value, β1-crystal content and β1-crystal heat of fusion of the obtained unstretched web sheet, and the thickness, porosity, Gurley air permeability, water vapor permeability, tensile strength and water pressure resistance of the stretched film are shown in Table 2.

Example 7

A stretched film was prepared in the same manner as in Example 6 except that the transverse direction stretch ratio and stretching rate were changed to 5.0 times and 16%/sec, respectively. The K value, β1-crystal content and β1-crystal heat of fusion of the obtained unstretched web sheet, and the thickness, porosity, Gurley air permeability, water vapor permeability, tensile strength and water pressure resistance of the stretched film are shown in Table 2.

Example 8

A stretched film was prepared in the same manner as in Example 1 except that PP7 was used as the raw compound. The K value, β1-crystal content and β1-crystal heat of fusion of the obtained unstretched web sheet, and the thickness, porosity, Gurley air permeability, water vapor permeability, tensile strength and water pressure resistance of the stretched film are shown in Table 2.

Example 9

A stretched film was prepared in the same manner as in Example 4 except that PP8 was used as the raw compound and the machine direction stretching temperature was changed to 80° C. The K value, β1-crystal content and β1-crystal heat of fusion of the obtained unstretched web sheet, and the thickness, porosity, Gurley air permeability, water vapor permeability, tensile strength and water pressure resistance of the stretched film are shown in Table 2.

Example 10

A stretched film was prepared in the same manner as in Example 7 except that PP9 was used as the raw compound. The K value, β1-crystal content and β1-crystal heat of fusion of the obtained unstretched web sheet, and the thickness, porosity, Gurley air permeability, water vapor permeability, tensile strength and water pressure resistance of the stretched film are shown in Table 3.

Example 11

A stretched film was prepared in the same manner as in Example 7 except that PP10 was used as the raw compound. The K value, β1-crystal content and β1-crystal heat of fusion of the obtained unstretched web sheet, and the thickness, porosity, Gurley air permeability, water vapor permeability, tensile strength and water pressure resistance of the stretched film are shown in Table 3.

Example 12

A stretched film was prepared in the same manner as in Example 1 except that PP11 was used as the raw compound and the machine direction stretching temperature was changed to 75° C. The K value, β1-crystal content and β1-crystal heat of fusion of the obtained unstretched web sheet, and the thickness, porosity, Gurley air permeability, water vapor permeability, tensile strength and water pressure resistance of the stretched film are shown in Table 3.

Example 13

A stretched film was prepared in the same manner as in Example 6 except that the contact time between the unstretched web sheet and the chill roll was extended to 21 seconds and the transverse direction stretching rate was changed to 48%/sec. The K value, β1-crystal content and β1-crystal heat of fusion of the obtained unstretched web sheet, and the thickness, porosity, Gurley air permeability, water vapor permeability, tensile strength and water pressure resistance of the stretched film are shown in Table 3.

Example 14

A stretched film was prepared in the same manner as in Example 6 except that the contact time between the unstretched web sheet and the chill roll was extended to 32 seconds and the transverse direction stretching rate was changed to 71%/sec. The K value, β1-crystal content and β1-crystal heat of fusion of the obtained unstretched web sheet, and the thickness, porosity, Gurley air permeability, water vapor permeability, tensile strength and water pressure resistance of the stretched film are shown in Table 3.

Example 15

A stretched film was prepared in the same manner as in Example 7 except that the surface temperature of the chill roll was changed to 115° C., and the contact time and machine direction stretch ratio were changed to 16 seconds and 4.5 times, respectively. The K value, β1-crystal content and β1-crystal heat of fusion of the obtained unstretched web sheet, and the thickness, porosity, Gurley air permeability, water vapor permeability, tensile strength and water pressure resistance of the stretched film are shown in Table 3.

Example 16

A stretched film was prepared in the same manner as in Example 15 except that the surface temperature of the chill roll and the contact time were changed to 125° C. and 18 seconds, respectively. The K value, β1-crystal content and β1-crystal heat of fusion of the obtained unstretched web sheet, and the thickness, porosity, Gurley air permeability, water vapor permeability, tensile strength and water pressure resistance of the stretched film are shown in Table 3.

Example 17

A stretched film was prepared in the same manner as in Example 6 except that the number of chill rolls was increased to three, the surface temperature of the first chill roll was held at 115° C. and that of the second and third chill rolls was held at 125° C., the holding time at each temperature was changed to 6 seconds and 15 seconds respectively, the machine direction stretching temperature was changed to 75° C. and the transverse direction stretching rate was changed to 142%/sea. The K value, β1-crystal content and β1-crystal heat of fusion of the obtained unstretched web sheet, and the thickness, porosity, Gurley air permeability, water vapor permeability, tensile strength and water pressure resistance of the stretched film are shown in Table 3.

Comparative Example 1

An unstretched web sheet was prepared in the same manner as in Example 14 except that PP12 was used as the raw compound. The K value, β1-crystal content and β1-crystal heat of fusion of the obtained unstretched web sheet are shown in Table 4. The preparation of a stretched film was then attempted in the same manner as in Example 7 using the obtained unstretched web sheet, but a uniform stretched film could not be obtained, due to remarkably uneven stretching during the machine direction stretching step.

Comparative Example 2

An unstretched web sheet was prepared in the same manner as In Example 14 except that PP13 was used as the raw compound. The K value, β1-crystal content and β1-crystal heat of fusion of the obtained unstretched web sheet are shown in Table 4. The preparation of a stretched film was then attempted in the same manner as in Example 7 using the obtained unstretched web sheet, but a uniform stretched film could not be obtained, due to remarkably uneven stretching during the machine direction stretching step.

Comparative Example 3

An unstretched web sheet was prepared In the same manner as in Example 1 except that PP14 was used as the raw compound. The K value, β1-crystal content and β1-crystal heat of fusion of the obtained unstretched web sheet are shown in Table 4. The preparation of a stretched film was then attempted in the same manner as in Example 7 using the obtained unstretched web sheet, but a uniform stretched film could not be obtained, due to breakage of the film during the transverse direction stretching step.

Comparative Example 4

An unstretched web sheet was prepared in the same manner as in Example 1 except that PP15 was used as the raw compound. The K value, β1-crystal content and β1-crystal heat of fusion of the obtained unstretched web sheet are shown in Table 4. The preparation of a stretched film was then attempted in the same manner as in Example 7 using the obtained unstretched web sheet, but a uniform stretched film could not be obtained, due to breakage of the film during the transverse direction stretching step.

Comparative Example 5

A stretched film was prepared in the same manner as in Example 7 except that PP16 was used as the raw compound. The K value, β1-crystal content and β1-crystal heat of fusion of the obtained unstretched web sheet, and the thickness, porosity, Gurley air permeability, water vapor permeability, tensile strength and water pressure resistance of the stretched film are shown in Table 4.

Comparative Example 6

An unstretched web sheet was prepared in the same manner as in Example 1 except that PP17 was used as the raw compound. The K value, β1-crystal content and β1-crystal heat of fusion of the obtained unstretched web sheet are shown in Table 4. The preparation of a stretched film was then attempted in the same manner as in Example 7 using the obtained unstretched web sheet, but a uniform stretched film could not be obtained, due to breakage of the film during the transverse direction stretching step.

Comparative Example 7

An unstretched web sheet was prepared in the same manner as in Example 1 except that PP18 was used as the raw compound. The K value, β1-crystal content and β1-crystal heat of fusion of the obtained unstretched web sheet are shown in Table 4. The preparation of a stretched film was then attempted in the same manner as in Example 7 using the obtained unstretched web sheet, but a uniform stretched film could not be obtained, due to breakage of the film during the transverse direction stretching step.

Comparative Example 8

A stretched film was prepared in the same manner as in Example 14 except that the surface temperature of the chill roll was changed to 110° C. The K value, β1-crystal content and β1-crystal heat of fusion of the obtained unstretched web sheet, and the thickness, porosity, Gurley air permeability, water vapor permeability, tensile strength and water pressure resistance of the stretched film are shown in Table 4.

Comparative Example 9

A stretched film was prepared in the same manner as in Example 14 except that the surface temperature of the chill roll was changed to 132° C. and the contact time was changed to 60 seconds. The K value, β1-crystal content and β1-crystal heat of fusion of the obtained unstretched web sheet, and the thickness, porosity, Gurley air permeability, water vapor permeability, tensile strength and water pressure resistance of the stretched film are shown in Table 4.

Comparative Example 10

A stretched film was prepared in the same manner as in Example 14 except that the contact time between the unstretched web sheet and the chill roll was changed to 8 seconds. The K value, β1-crystal content and β1-crystal heat of fusion of the obtained unstretched web sheet, and the thickness, porosity, Gurley air permeability, water vapor permeability, tensile strength and water pressure resistance of the stretched film are shown in Table 4.

TABLE 1

| | Raw resin | Raw compound | | | | | | | | |
|---|---|---|---|---|---|---|---|---|---|---|
| | | PP1 | PP2 | PP3 | PP4 | PP5 | PP6 | PP7 | PP8 | PP9 |
| Composition (wt. %) | A1 | 10 | 16 | 16 | 20 | 20 | 23 | 25 | 30 | — |
| | A2 | — | — | — | — | — | — | — | — | 33 |
| | A3 | — | — | — | — | — | — | — | — | — |
| | B1 | 45 | 21 | 42 | — | 20 | 44 | 50 | — | — |
| | B2 | — | — | — | — | — | — | — | — | 33 |
| | C1 | 45 | 63 | 42 | 80 | 60 | 33 | 25 | 70 | 34 |
| | C2 | — | — | — | — | — | — | — | — | — |
| MFR of resin mixture (g/10 min) | | 3.1 | 3.3 | 3.6 | 3.7 | 3.4 | 2.5 | 2.3 | 3.5 | 3.4 |
| Ethylene content of resin mixture (wt. %) | | 4.5 | 4.5 | 4.5 | 4.4 | 4.5 | 4.5 | 4.6 | 4.4 | 4.5 |

| | Raw resin | Raw compound | | | | | | | | |
|---|---|---|---|---|---|---|---|---|---|---|
| | | PP10 | PP11 | PP12 | PP13 | PP14 | PP15 | PP16 | PP17 | PP18 |
| Composition (wt. %) | A1 | — | — | 100 | — | — | — | 35 | 10 | — |
| | A2 | 33 | — | — | — | — | — | — | — | — |
| | A3 | — | 20 | — | — | — | — | — | — | — |
| | B1 | — | — | — | — | — | — | 65 | — | 25 |
| | B2 | 33 | — | — | 100 | — | — | — | — | — |
| | C1 | — | — | — | — | 100 | — | — | 90 | 75 |
| | C2 | 34 | 80 | — | — | — | 100 | — | — | — |
| MFR of resin mixture (g/10 min) | | 2.7 | 2.7 | 0.5 | 2.9 | 6.5 | 4.2 | 1.4 | 4.1 | 4.2 |
| Ethylene content of resin mixture (wt. %) | | 5.7 | 6.2 | 4.4 | 0.0 | 4.4 | 7.8 | 4.6 | 4.4 | 4.6 |

TABLE 2

| | | Example | | | | | | | | |
|---|---|---|---|---|---|---|---|---|---|---|
| Item | | 1 | 2 | 3 | 4 | 5 | 6 | 7 | 8 | 9 |
| Raw compound | | PP1 | PP2 | PP3 | PP4 | PP5 | PP6 | PP6 | PP7 | PP8 |
| Cast conditions | | | | | | | | | | |
| Chill roll temp. (° C) | | 120 | 120 | 120 | 120 | 120 | 120 | 120 | 120 | 120 |
| Contact time with chill roll (sec) | | 12 | 12 | 12 | 12 | 12 | 12 | 12 | 12 | 12 |
| Characteristics of unstretched web sheet | | | | | | | | | | |
| K value | | 0.95 | 0.94 | 0.94 | 0.96 | 0.93 | 0.95 | 0.95 | 0.93 | 0.94 |
| β1-crystal content (%) | | 72 | 70 | 70 | 71 | 72 | 71 | 71 | 70 | 71 |
| β1-crystal heat of fusion (J/g) | | 56 | 58 | 56 | 57 | 57 | 58 | 58 | 57 | 56 |
| Stretching conditions | | | | | | | | | | |
| Machine direction stretching | Temp. (° C) | 80 | 80 | 75 | 85 | 80 | 80 | 80 | 80 | 80 |
| | Ratio | 4.0 | 4.0 | 4.0 | 4.0 | 4.0 | 4.0 | 4.0 | 4.0 | 4.0 |
| Transverse direction stretching | Temp. (° C) | 140 | 140 | 140 | 145 | 140 | 140 | 140 | 140 | 145 |
| | Rate (%/sec) | 24 | 24 | 26 | 16 | 24 | 24 | 16 | 24 | 16 |
| | Ratio (times) | 7.5 | 7.5 | 8.0 | 5.0 | 7.5 | 7.5 | 5.0 | 7.5 | 5.0 |

TABLE 2-continued

| | Example | | | | | | | | |
|---|---|---|---|---|---|---|---|---|---|
| Item | 1 | 2 | 3 | 4 | 5 | 6 | 7 | 8 | 9 |
| Characteristics of stretched film | | | | | | | | | |
| Thickness (μm) | 19 | 17 | 14 | 22 | 17 | 17 | 26 | 16 | 21 |
| Porosity (%) | 39 | 37 | 32 | 44 | 36 | 36 | 50 | 34 | 40 |
| Gurley air permeability (sec/100 cc) | 900 | 900 | 1300 | 800 | 1300 | 1200 | 800 | 1500 | 1000 |
| Water vapor permeability (g/m$^2$ · 24 h) | 4700 | 4600 | 4200 | 4800 | 4400 | 4700 | 4800 | 3700 | 4600 |
| Tensile strength (MPa) Longitudinal | 70 | 73 | 72 | 67 | 70 | 76 | 73 | 80 | 67 |
| Tensile strength (MPa) Transverse | 77 | 76 | 89 | 65 | 76 | 87 | 77 | 96 | 69 |
| Water pressure resistance (kPa) | >200 | >200 | 180 | 190 | >200 | >200 | >200 | >200 | >200 |

TABLE 3

| | Example | | | | | | | |
|---|---|---|---|---|---|---|---|---|
| Item | 10 | 11 | 12 | 13 | 14 | 15 | 16 | 17 |
| Raw compound | PP9 | PP10 | PP11 | PP6 | PP6 | PP6 | PP6 | PP6 |
| Cast conditions | | | | | | | | |
| Chill roll temp. (° C) | 120 | 120 | 120 | 120 | 120 | 115 | 125 | 115/120 |
| Contact time with chill roll (sec) | 12 | 12 | 12 | 21 | 32 | 16 | 21 | 6/15 |
| Characteristics of unstretched web sheet | | | | | | | | |
| K value | 0.95 | 0.94 | 0.95 | 0.95 | 0.96 | 0.95 | 0.93 | 0.96 |
| β1-crystal content (%) | 72 | 69 | 70 | 76 | 79 | 67 | 68 | 82 |
| β1-crystal heat of fusion (J/g) | 58 | 56 | 66 | 62 | 65 | 54 | 54 | 67 |
| Stretching conditions | | | | | | | | |
| Machine direction stretching Temp. (° C) | 80 | 80 | 75 | 80 | 80 | 80 | 80 | 75 |
| Machine direction stretching Ratio | 4.0 | 4.0 | 4.0 | 4.0 | 4.0 | 4.5 | 4.5 | 4.0 |
| Transverse direction stretching Temp. (° C) | 140 | 140 | 140 | 140 | 140 | 140 | 140 | 140 |
| Transverse direction stretching Rate (%/sec) | 16 | 16 | 24 | 48 | 71 | 16 | 16 | 142 |
| Transverse direction stretching Ratio (times) | 5.0 | 5.0 | 7.5 | 7.5 | 7.5 | 5.0 | 5.0 | 7.5 |
| Characteristics of stretched film | | | | | | | | |
| Thickness (μm) | 17 | 19 | 15 | 15 | 16 | 14 | 15 | 15 |
| Porosity (%) | 29 | 39 | 32 | 34 | 32 | 32 | 30 | 35 |
| Gurley air permeability (sec/100 cc) | 2100 | 1700 | 2400 | 1100 | 1400 | 2500 | 3000 | 1300 |
| Water vapor permeability (g/m$^2$ · 24 h) | 2800 | 3100 | 2600 | 4900 | 4500 | 2800 | 2200 | 4800 |
| Tensile strength (MPa) Longitudinal | 65 | 66 | 62 | 73 | 74 | 76 | 76 | 76 |
| Tensile strength (MPa) Transverse | 69 | 63 | 63 | 90 | 92 | 79 | 78 | 91 |
| Water pressure resistance (kPa) | 170 | 190 | 150 | >200 | >200 | >200 | >200 | >200 |

TABLE 4

| | Comparative example | | | | | | | | | |
|---|---|---|---|---|---|---|---|---|---|---|
| Item | 1 | 2 | 3 | 4 | 5 | 6 | 7 | 8 | 9 | 10 |
| Raw compound | PP12 | PP13 | PP14 | PP15 | PP16 | PP17 | PP18 | PP6 | PP6 | PP6 |
| Cast conditions | | | | | | | | | | |
| Chill roll temp. (° C) | 120 | 120 | 120 | 120 | 120 | 120 | 120 | 110 | 132 | 120 |
| Contact time with chill roll (sec) | 32 | 32 | 12 | 12 | 12 | 12 | 12 | 32 | 60 | 8 |
| Characteristics of unstretched web sheet | | | | | | | | | | |
| K value | 0.94 | 0.96 | 0.94 | 0.95 | 0.96 | 0.96 | 0.93 | 0.96 | 0.95 | 0.93 |
| β1-crystal content (%) | 79 | 80 | 70 | 66 | 71 | 68 | 71 | 63 | 59 | 61 |
| β1-crystal heat of fusion (J/g) | 64 | 67 | 58 | 53 | 57 | 55 | 56 | 48 | 45 | 47 |

TABLE 4-continued

| Item | | Comparative example | | | | | | | | | |
|---|---|---|---|---|---|---|---|---|---|---|---|
| | | 1 | 2 | 3 | 4 | 5 | 6 | 7 | 8 | 9 | 10 |
| Stretching conditions | | | | | | | | | | | |
| Machine direction stretching | Temp. (°C) | 90 | 90 | 80 | 80 | 80 | 80 | 80 | 80 | 80 | 80 |
| | Ratio | 4.0 | 4.0 | 4.0 | 4.0 | 4.0 | 4.0 | 4.0 | 4.0 | 4.0 | 4.0 |
| Transverse direction stretching | Temp. (°C) | 140 | 140 | 140 | 140 | 140 | 140 | 140 | 140 | 140 | 140 |
| | Rate (%/sec) | 16 | 16 | 16 | 16 | 16 | 16 | 16 | 16 | 16 | 16 |
| | Ratio (times) | 5.0 | 5.0 | 5.0 | 5.0 | 5.0 | 5.0 | 5.0 | 5.0 | 5.0 | 5.0 |
| Characteristics of stretched film | | | | | | | | | | | |
| Thickness (μm) | | Uneven Stretching | Uneven Stretching | Breakage | Breakage | 20 | Breakage | Breakage | 18 | 17 | 18 |
| Porosity (%) | | | | | | 40 | | | 36 | 35 | 35 |
| Gurley air permeability (sec/100 cc) | | | | | | >20000 | | | 8500 | 18000 | 9600 |
| Water vapor permeability (g/m² · 24 h) | | | | | | 900 | | | 1800 | 1200 | 1800 |
| Tensile strength (MPa) | Longitudinal | | | | | 90 | | | 75 | 76 | 74 |
| | Transverse | | | | | 89 | | | 77 | 75 | 79 |
| Water pressure resistance (kPa) | | | | | | >200 | | | >200 | >200 | >200 |

EFFECTS OF THE INVENTION

With the present invention, it is possible, in the manufacture of a porous film composed of a stretched β-crystal-based polypropylene, to maintain a good balance between the air permeability of the stretched film and its tendency toward breakage during stretching, which was a problem in the past. This makes it possible to industrially easily manufacture under practical conditions a porous polypropylene film with excellent breathability and continuous through-pores.

The thus obtained stretched film of the present invention has not only excellent breathability and water vapor permeability, but also excellent leakage prevention and mechanical strength, and is very useful as a material for use in various fields, such as moisture-permeable waterproof garments, sanitary products, paper diapers and other such absorbent articles, hygienic merchandise, construction materials, various packaging materials, synthetic paper, filtration membranes, separation membranes, battery separators, agricultural multi-sheets, and so forth. Among the above-mentioned products, absorbent articles using the porous film of the present invention as a backsheet have no problems with regard to urinary incontinence or breakage of the backside material of the film when attaching or detaching a closure tape, and the articles have excellent texture and can be comfortably worn without causing a stuffy feeling.

What is claimed is:

1. A porous polypropylene film with excellent breathability and continuous through-pores and made of a propylene-based resin composition comprising
    (I) (i) a propylene-ethylene copolymer having an ethylene content of 3.0 to 7.0 wt. % and a melt flow rate (MFR, JIS K-6557) measured at 230° C. of 2.0 to 4.0 g/10 min
    or
    (ii) a polypropylene-based resin mixture containing a propylene-ethylene copolymer, the mixture having an ethylene content of 3.0 to 7.0 wt. % and a melt flow rate (MFR, JIS K-6857) measured at 230° C. of 2.0 to 4.0 g/10 min
    (II) a beta-crystal nucleating agent;
    the film having a porosity of 20 to 80%, a Gurley air permeability of 5,000 sec/100 cc or lower as measured according to JIS P-8117, a water vapor permeability of 2.000 g/m²·24 h or higher as measured according to JIS Z-0208 and a water pressure resistance of 74 kPa or higher as measured according to JIS L-1092 except that an aqueous surfactant solution is used instead of pure water.

2. The porous polypropylene film according to claim 1, which has a film thickness of 5 to 50 microns and a mechanical strength of 40 MPa or higher as measured according to JIS K-7127.

3. The porous polypropylene film according to claim 1, which is prepared by stretching an unstretched web sheet wherein the proportion of thermally stable β crystals (β1 crystals) relative to the total amount of all crystals is 65% or higher, and the β1-crystal heat of fusion per unit weight of the unstretched web sheet is 50 J/g or higher, as determined by differential scanning calorimetry (DSC).

4. The porous polypropylene film according to claim 1, wherein at least one component of the polypropylene-based resin mixture containing a propylene-ethylene copolymer is a polypropylene resin having a weight average molecular weight (Mw) of $10^5$ to $10^6$ as determined by gel permeation chromatography (GPC) and a melt flow rate (MFR, JIS K-6857) measured at 230° C. of 0.5 to 10.0 g/10 min.

5. The porous polypropylene film according to claim 1, wherein the polypropylene-based resin mixture containing a propylene-ethylene copolymer is composed of a mixture of at least two members of polypropylene-based resins selected from the following resins (A), (B) and (C):
    (A) a polypropylene-based resin having an MFR of 0.1 to 2.0 g/10 min;
    (B) a polypropylene-based resin having an MFR of more than 2.0 g/10 min and less than 4.0 g/10 min;
    (C) a polypropylene-based resin having an MFR of 4.0 to 10.0 g/10 min;
    the mixture having an ethylene content of 3.0 to 7.0 wt. % and a melt flow rate (MFR, JIS K-6857) measured at 230° C. of 2.0 to 4.0 g/10 min; and at least one component of the mixture being a propylene-ethylene copolymer.

6. The porous polypropylene film according to claim 5, wherein the polypropylene-based resin mixture comprises 10 to 35 wt. % of resin (A), 0 to 50 wt. % of resin (B) and 25 to 80 wt % of resin (C).

7. The porous polypropylene film according to claim 1, wherein the beta-crystal nucleating agent is an amide compound represented by formula (1)

$$R^2\text{—NHCO—}R^1\text{—CONH—}R^3 \quad (1)$$

wherein $R^1$ is a $C_{1-24}$ saturated or unsaturated aliphatic dicarboxylic acid residue, a $C_{4-28}$ saturated or unsaturated alicyclic dicarboxylic acid residue, or a $C_{6-28}$ aromatic dicarboxylic acid residue, $R^2$ and $R^3$ are the same or different and each represents a $C_{3-18}$ cycloalkyl group, or a group of formula (a), formula (b), formula (c) or formula (d)

wherein $R^4$ is a hydrogen atom, a $C_{1-12}$ straight-chain or branched-chain alkyl group, a $C_{6-10}$ cycloalkyl group, or phenyl group, $R^5$ is a $C_{1-12}$ straight-chain or branched-chain alkyl group, and $R^6$ and $R^7$ are the same or different and each represents a $C_{1-4}$ straight-chain or branched-chain alkylene group.

8. A backsheet for absorbent articles comprising the porous polypropylene film with excellent breathability and continuous through-pores according to any one of claims 1 to 7.

9. An absorbent article comprising a liquid-permeable topside material, a liquid-impervious backside material and an absorbing material interposed between the topside material and the backside material, wherein the backside material comprises the backsheet according to claim 8.

10. The absorbent article according to claim 9, wherein said absorbent article is a hygienic article.

11. The hygienic article according to claim 10, wherein said hygienic article is a member selected from the group consisting of a disposable diaper, a pants-shaped diaper, a sanitary napkin, and an incontinence pad.

12. A process for producing the porous polypropylene film with excellent breathability and continuous through-pores according to claim 1, wherein the process comprises the step of stretching an unstretched web sheet made of a polypropylene-based resin composition comprising (I) (i) a propylene-ethylene copolymer having an ethylene content of 3.0 to 7.0 wt. % and a melt flow rate (MFR, JIS K-6857) measured at 230° C. of 2.0 to 4.0 g/10 min or (ii) a polypropylene-based resin mixture containing a propylene-ethylene copolymer, the mixture having an ethylene content of 3.0 to 7.0 wt. % and a melt flow rate (MFR, JIS K-6857) measured at 230° C. of 2.0 to 4.0 g/10 min and (II) a β-crystal nucleating agent;

the unstretched web sheet having a thermally stable β-crystal (β1-crystal) content of 65% or higher, and a β1-crystal heat of fusion per unit weight of the unstretched web sheet of 50 J/g or higher, as determined by differential scanning calorimetry (DSC).

13. The process for producing the porous polypropylene film according to claim 12, wherein the unstretched web sheet is made of a polypropylene-based resin composition comprising (I) a polypropylene-based resin mixture containing a propylene-ethylene copolymer and having an ethylene content of 3–0 to 7.0 wt. % and a melt flow rate (MFR, JIS K-6857) measured at 230° C. of 2.0 to 4.0 g/10 min and (II) a beta-crystal nucleating agent; and at least one component of the polypropylene-based resin mixture is a polypropylene-based resin having a weight average molecular weight (Mw) of $10^5$ to $10^6$ as determined by gel permeation chromatography (GPC) and a melt flow rate (MFR, JIS K-6857) measured at 230° C. of 0.5 to 10.0 g/10 min.

14. The process for producing the porous polypropylene film according to claim 12, wherein the unstretched web sheet is formed by the steps of cooling and solidifying a molten sheet of the polypropylene-based resin composition extruded from a T-die, in the form of a sheet, under the following crystallization conditions:

110° C.<crystallization temperature ($Tcr$, ° C.)≦130° C.; and shortest crystallization holding time ($tmin$ (sec))≦crystallization holding time ($tcr$, sec)<60 seconds, wherein tmin (sec) is calculated by the following equations:

in the case of $Tcr<120°$ C., $tmin(sec)=0.1(120-Tcr)^2+10$; or in the case of $Tcr≧120°$ C., $tmin(sec)=0.3(120-Tcr)^2+10$.

15. The process for producing the porous polypropylene film according to claim 14, wherein the crystallization holding time condition is satisfied by crystallizing the molten sheet of the polypropylene-based resin composition extruded from a T-die, using a multistage chill roll having a plurality of chill-rolls or using one chill-roll in combination with a heat source other than a chill roll.

16. The process for producing the porous polypropylene film according to claim 12, wherein the stretching step is successive biaxial stretching.

17. The process for producing the porous polypropylene film according to claim 16, wherein the successive biaxial stretching step is carried out by conducting machine direction stretching at a ratio of 4 to 5 times at a stretching temperature of 70° C. to 90° C. and then transverse direction stretching at a ratio of 5 to 10 times at a stretching temperature of 135° C. to 155° C. and at a stretching rate of 10 to 300%/sec.

* * * * *